United States Patent
Möller et al.

(10) Patent No.: US 6,768,317 B2
(45) Date of Patent: Jul. 27, 2004

(54) METHOD OF AND APPARATUS FOR TESTING A FIRST MATERIAL FOR POTENTIAL PRESENCE OF SECOND MATERIALS

(75) Inventors: Henning Möller, Hamburg (DE); Jorg Tobias, Drage (DE)

(73) Assignee: Hauni Maschinenbau AG, Hamburg (DE)

( * ) Notice: Subject to any disclaimer, the term of this patent is extended or adjusted under 35 U.S.C. 154(b) by 83 days.

(21) Appl. No.: 10/034,258

(22) Filed: Jan. 3, 2002

(65) Prior Publication Data

US 2002/0121906 A1 Sep. 5, 2002

(30) Foreign Application Priority Data

Jan. 9, 2001 (DE) ............................................ 101 00 664

(51) Int. Cl.[7] .................... G01R 27/04; G01R 27/32; A24C 5/39
(52) U.S. Cl. .................... 324/637; 324/640; 131/109.2; 131/905
(58) Field of Search ................................ 324/637, 638, 324/639, 640, 633, 634, 636; 131/108, 905, 109.2, 84.1

(56) References Cited

U.S. PATENT DOCUMENTS

| | | | |
|---|---|---|---|
| 4,281,670 A | | 8/1981 | Heitmann et al. |
| 4,412,505 A | | 11/1983 | Haiisler et al. |
| 4,514,680 A | | 4/1985 | Heikkilä et al. |
| 4,707,652 A | | 11/1987 | Lowitz |
| 4,942,363 A | * | 7/1990 | Lowitz ................ 324/638 |
| 5,016,653 A | * | 5/1991 | Lassiter ................ 131/84.1 |
| 5,476,108 A | * | 12/1995 | Dominguez et al. ....... 131/108 |
| 5,736,864 A | | 4/1998 | Möller |
| 6,163,158 A | | 12/2000 | Möller et al. |

FOREIGN PATENT DOCUMENTS

| | | |
|---|---|---|
| DE | 19625944 | 1/1997 |
| DE | 19705260 | 8/1997 |
| DE | 19806125 | 8/1999 |
| DE | 19854550 | 5/2000 |
| EP | 0 337 623 | 10/1989 |
| EP | 0 791 823 | 8/1997 |
| WO | WO 00/09983 | 2/2000 |
| WO | WO 01/20311 | 3/2001 |

OTHER PUBLICATIONS

Patent Abstract of Japan, vol. 012, No. 255 (P–732), JP 63 045547, Feb. 26, 1988.

\* cited by examiner

*Primary Examiner*—N. Le
*Assistant Examiner*—Timothy J. Dole
(74) *Attorney, Agent, or Firm*—Venable LLP; Robert Kinberg; Chad C. Anderson

(57) ABSTRACT

A method of detecting impurities in a mass, such as detecting metallic and/or plastic particles in a stream of tobacco particles or filter material for tobacco smoke, includes the steps of moving the mass relative to a microwave field and/or vice versa, and analyzing the influence of the mass upon the microwave field. The analyzing step involves simultaneously measur- the actual values of a first and a second parameter of the microwave field, ascertaining the presence or absence of those changes of the parameters which are attributable to the presence of impurities in the mass, determining whether or not the changes are within an acceptable range, and generating signals for segregation of impurities-containing portions of the mass from the other portions when the changes are outside of the acceptable range.

20 Claims, 5 Drawing Sheets

Legend
3: generator
11: evaluating circuit
22: rectifier diode
23: demodulator
24: frequency regulator
28: first computer
31: second computer
31a: ejector
33: memory Legend
3: generator
11: evaluating circuit
22: rectifier diode
23: demodulator
24: frequency regulator
28: first computer
31: second computer
31a: ejector
33: memory

METHOD OF AND APPARATUS FOR TESTING A FIRST MATERIAL FOR POTENTIAL PRESENCE OF SECOND MATERIALS

CROSS-REFERENCE TO RELATED CASES

The present application claims the priority of the commonly owned copending German patent application Serial No. 101 00 664.0 filed Jan. 9, 2001. The disclosure of the above-referenced German patent application, as well as that of each US and foreign patent and patent application identified in the specification of the present application, is incorporated herein by reference.

BACKGROUND OF THE INVENTION

The present invention relates to improvements in methods of and in apparatus for testing materials for the presence or absence of impurities and/or other foreign matter, for example, to methods of and to apparatus for detecting the presence (if any) of one or more second (foreign) materials or substances in a body or mass which consists primarily of a first (particulate) material. More particularly, the present invention relates to improvements in methods of and in apparatus for monitoring or testing or examining a mass normally consisting of a first material for the presence or absence of one or more second materials (hereinafter often called impurities for short) by resorting to a microwave field which is influenced by the impurities contained in the first material when the impurities-containing first material is introduced into the range of the microwave field.

An example of a first material which is or which might be likely to contain one or more impurities (such as metallic or plastic particles) is tobacco, e.g., the so-called rod-like filler of a running continuous cigarette rod or the fillers of discrete cigarettes running endwise or sideways in a cigarette making and/or processing machine. It is important to detect the presence of impurities in tobacco which is processed in modern high-speed machines or apparatus designed to turn out and/or to automatically process huge quantities of smokers' products per unit of time. Certain machines or apparatus of such character are set up to subject a running mass or flow or a plurality of discrete masses or flows of comminuted natural, artificial and/or reconstituted tobacco to a series of successive treatments by resorting to belt conveyors, chain conveyors or analogous transporting means which advance tobacco between various stations or units, storage facilities and/or others.

It is inevitable or at least highly likely that the treatment of tobacco and/or of tobacco-containing products or similar products or commodities of the tobacco processing industry (e.g., filter material for tobacco smoke which is processed in filter rod making, filter cigarette making and similar units) results in or causes the introduction of impurities into tobacco, filter material and/or other primary or first materials. The presence of metallic particles, plastic particles and/or other impurities in plain or filter cigarettes and/or other finished smokers' products can adversely influence the appearance, the taste, the rate of combustion and/or other characteristics of such products. Therefore, the relevant industries are continuously seeking to arrive at methods and apparatus for reliably detecting impurities in smokers' products, and especially at improved methods and apparatus which can be put to use in modern high-speed machines (such as cigarette or filter cigarette making machines) that are capable of detecting impurities and/or of preventing introduction of impurities without necessitating a deceleration of such machines and without adversely affecting the appearance, the taste, the quality and/or other desirable characteristics or parameters of the products. The same holds true for the methods of and for the apparatus for mass-producing numerous other commodities, e.g., the aforementioned filter rods for tobacco smoke, filter rod sections and/or others.

Conventional undertakings to detect impurities in a primary or first material include numerous optical processes one step of which involves advancing the primary material along a path wherein the material is converted into a thin (single-stratum) layer. The exposed surface of the layer is photographed by one or more cameras and the thus obtained pictures are processed for the purpose of detecting and pinpointing foreign bodies (impurities) preparatory to their removal or expulsion from the layer. A drawback of such processes is that the equipment which is necessary for their practice is bulky and that such equipment can be put to use only during initial processing, e.g., during treatment of tobacco or filter material prior to entry into a cigarette rod making, filter rod making or an analogous machine. Consequently, the just described processes and apparatus cannot be resorted to for the detection of impurities which enter the primary material in a cigarette making, filter rod making or analogous machine, namely subsequent to confinement of the fillers of cigarettes, filter mouthpieces or the like in tubular wrappers consisting of or containing cigarette paper, artificial cork, tipping paper or the like.

In order to overcome the shortcomings of processes which are effective only during preliminary treatment of primary material (e.g., during transport of tobacco or filter material for tobacco smoke into a cigarette rod making or filter rod making machine), many machines of such character embody or are combined or associated with (a) suitable sifting devices which are capable of removing from the flow (stream) of tobacco or from the flow (tow) of filter material for tobacco smoke entering a cigarette maker or a filter rod maker certain heavier particles (such as tobacco ribs) and/or (b) with metal detectors (e.g., magnets) capable of detecting and/or detecting and segregating defective articles such as plain or filter cigarettes or filter rod sections. A drawback of the just discussed undertakings is that they can detect and/or remove only certain types of impurities so that, unless combined with sifting or the like, each such undertaking can ensure only the detection and segregation of a relatively low percentage of all impurities.

Certain additional presently known processes and apparatus for the detection of impurities rely upon the utilization of microwaves which are resorted to for the monitoring of specific parameters (such as the density and/or the moisture content) of finished or semifinished smokers' products, for example, a continuous cigarette rod and/or discrete plain or filter cigarettes. An advantage of such undertakings is that they can furnish information with a very high degree of accuracy. Their effectiveness is attributable to the fact that the primary material (such as tobacco) is a satisfactory dielectric and highly hygroscopic so that it can contain a relatively high percentage of water (e.g., between about 10 and 20 percent by weight). In addition, water is also a highly satisfactory dielectric substance and, due to pronounced mobility of the molecular dipoles, exhibits a high loss factor at microwave frequencies. Such characteristics enable tobacco to exert a pronounced influence upon a microwave field, and this influence renders it possible to adequately distinguish between water and dry tobacco. Reference may be had to the disclosure in U.S. Pat. No. 4,707,652 granted Nov. 17, 1987 to Lowitz for "IMPURITY DETECTOR MEASURING PARALLEL POLARIZED SCATTERED ELECTROMAGNETIC RADIATION". The method which is disclosed in this patent involves a determination of abnormalities in spatial scattering of a microwave field by a tobacco sample to thus detect the presence or absence of impurities, such as metallic or plastic substances. The patented process is suitable for experimental practice in a laboratory, and its operation is satisfactory as long as the relative speed between the monitoring equipment and a sample is relatively low, i.e., such process cannot be resorted to in a high-speed machine, e.g., in a cigarette maker which turns out cigarettes in the range of up to 20,000 per minute.

OBJECTS OF THE INVENTION

An object of the invention is to provide a novel and improved method of at least detecting but preferably of detecting and segregating impurities which are randomly distributed in a primary (first) material or substance.

Another object of the invention is to provide a process which can be practiced by resorting to a relatively simple and inexpensive but highly reliable apparatus.

A further object of the instant invention is to provide a method which can be practiced while the material to be monitored for the presence of impurities is being advanced at a low speed as well as when the relative movement between such material and the detecting instrumentalities takes place at a high or extremely high speed.

An additional object of the invention is to provide a method which can be practiced for the detection of one or more types of impurities in shaped smokers' products (such as plain or filter cigarettes, continuous cigarette rods, continuous rods containing filter material for tobacco smoke and/or filter rod sections) being turned out or processed in modern high-speed machines such as cigarette makers, filter cigarette makers, filter rod makers and/or others.

Still another object of the present invention is to provide a method which can be resorted to for the detection of presence of one or more impurities in rod-shaped products of the tobacco processing industry with a heretofore unmatched degree of accuracy and reliability.

A further object of the invention is to provide a method which can be practiced upon completion of relatively simple and inexpensive modifications of existing types of machines for the making of smokers' products including plain cigarettes, cigarillos, cigars or the like, filter cigarettes, cigars, cigarillos or the like, filter mouthpieces for tobacco smoke, continuous tobacco-containing rods, continuous rods containing filter material for tobacco smoke and the like.

Another object of our invention is to provide a novel and improved apparatus for the practice of the above outlined method.

An additional object of the present invention is to provide an apparatus which can be combined with or incorporated into existing mass producing machines or production lines for the making of smokers' products, components of smokers' products as well as many other products which may but need not have any relationship with smoking.

Still another object of the invention is to provide a novel and improved impurities detecting apparatus which utilizes electromagnetic radiation.

A further object of the present invention is to provide a novel and improved method which, in addition to being capable of detecting impurities (such as foreign objects in a wrapped or unwrapped mass or flow of solid particles) can simultaneously serve for monitoring other (such as desirable) characteristics of commodities which are being turned out at a high or extremely high rate or frequency.

Another object of the invention is to provide an apparatus which treats the materials or commodities gently, which occupies a small amount of space in a manufacturing plant, which can be put to use in conjunction with existing types of tobacco processing and related or unrelated plants, and which contributes significantly to the appearance as well as to the taste and/or other desirable characteristics of the ultimate products.

An additional object of the invention is to provide a novel and improved cigarette making or filter rod making machine which embodies the above outlined apparatus.

SUMMARY OF THE INVENTION

One feature of the present invention resides in the provision of a method of testing a mass consisting at least primarily (i.e., at times primarily and at times exclusively) of a first material (e.g., shredded tobacco) for the presence of at least one second material (e.g., impurities including particles of metallic material, plastic material or the like). The improved method comprises the steps of establishing and maintaining a microwave field, introducing the mass into the range of the microwave field so that the microwave field is influenced by the mass (the introducing step can include moving the mass relative to the microwave field and/or vice versa), and analyzing the influence of the mass upon the microwave field. The analyzing step includes simultaneously measuring the actual values of a first and a second characteristic of the microwave field, selecting an acceptable value range for the actual values, ascertaining whether the actual values are within the acceptable range, and generating signals when the actual values are outside of the acceptable range.

The acceptable range encompasses or should encompass measured values of first and second characteristics of the microwave field when such field is influenced by a mass which contains only the first material.

The actual values are outside of the acceptable range—to thus initiate the generation of signals—when the mass which is being introduced into the range of the microwave field contains the at least one second material.

The mass can include or constitute a stream or flow, and the introducing step of such method can include moving the stream through the microwave field.

For example, the mass can consist at least of the first material, of a wrapper (such as a tubular wrapper) for the first material, and also possibly or potentially of at least one second material which, if present in the mass, is or can be randomly distributed in the first material.

As already mentioned hereinbefore, the first material is or can be a material of the tobacco processing industry, e.g., a smokable material (such as shredded tobacco) and/or filter material (such as acetate fibers, charcoal, etc.) for tobacco smoke.

The improved method can further comprise the steps of conveying the mass through the microwave field along a predetermined path, subdividing the mass in the path into a plurality of sections, and utilizing the signals (if and when generated) to segregate from the path those sections of the mass the introduction of which into the range of the microwave field has resulted in the generation of signals. The mass which is being conveyed along the aforementioned path can include the filler of a continuous cigarette rod or the filler of a continuous filter rod, and the subdividing step can include subdividing the cigarette rod or the filter rod into plain cigarettes or filter rod sections of unit or multiple unit length. The segregating step can include expulsion of plain cigarettes or filter rod sections from the path by resorting to a pneumatic, a mechanical or any other suitable segregating device.

Alternatively, the introducing step can include imparting to the mass the shape of a stream and conveying the stream in a predetermined direction along a path extending through the microwave field, confining the stream in a wrapping material upstream of the microwave field (as seen in the predetermined direction), and subdividing the wrapping material and the first material therein into a succession of discrete sections (e.g., plain cigarettes or filter rod sections of unit length or multiple unit length). When a signal is generated, it is utilized to segregate from the path discrete sections which contain second material. As already mentioned hereinbefore, each discrete section can include a rod-shaped smokers' product having a rod-like filler and a tubular wrapper for the filler. The wrapper can consist of cigarette paper, imitation cork, so-called tipping paper which is utilized to unite cigarettes with filter mouthpieces and/or others.

The step of selecting an acceptable value range for the actual values can include introducing into the microwave field a sample mass which is devoid of the at least one second material (i.e., which consists exclusively of first material), examining the sample mass while such sample mass is within the microwave field, and utilizing the examining step to select the acceptable value range.

In accordance with an advantageous additional feature of the invention, the improved method can include the step of utilizing the measured actual values of the first and second characteristics of the microwave field for a determination of a characteristic of the mass other than potential presence of at least one second material. If the first material contains tobacco, the tobacco characteristic other than the potential presence of one or more second materials therein can include the density and/or the moisture content of tobacco.

Another feature of the present invention resides in the provision of an apparatus for testing a mass consisting at least primarily (but frequently or normally exclusively) of a first material for the presence of impurities (materials other than the first material). The improved apparatus comprises means for establishing and maintaining a microwave field, means for moving the mass and/or the microwave field relative to each other so that the microwave field is influenced by the mass, and means for analyzing the influence of the mass upon the microwave field. The analyzing means can include means for simultaneously measuring the actual values of first and second characteristics of the microwave field, means for selecting an acceptable value range for the actual ranges, means for ascertaining whether the actual values are within the acceptable range, and means for generating signals when the actual values are outside of the acceptable range as a result of the influence of impurities upon the microwave field.

The moving means can include means for moving an elongated flow of the mass along an elongated path a portion of which extends through the microwave field.

The apparatus can further comprise means for segregating (in respose to the signals) from the mass those portions which contain one or more impurities (e.g., metallic and/or plastic articles or particles).

The first material is or can be a material of the tobacco processing industry.

The apparatus can further comprise means for processing the actual values for the determination of one, two or more characteristics (such as the density and/or the moisture content) of first material other than the presence or absence of impurities.

The novel features which are considered as characteristic of the invention are set forth in particular in the appended claims. The improved apparatus itself, however, both as to its construction and the modes of assembling, installing and utilizing the same, together with numerous additional important and advantageous features and attributes thereof, will be best understood upon perusal of the following detailed description of certain presently preferred specific embodiments with reference to the accompanying drawing.

DESCRIPTION OF PREFERRED EMBODIMENTS

Figure 1:
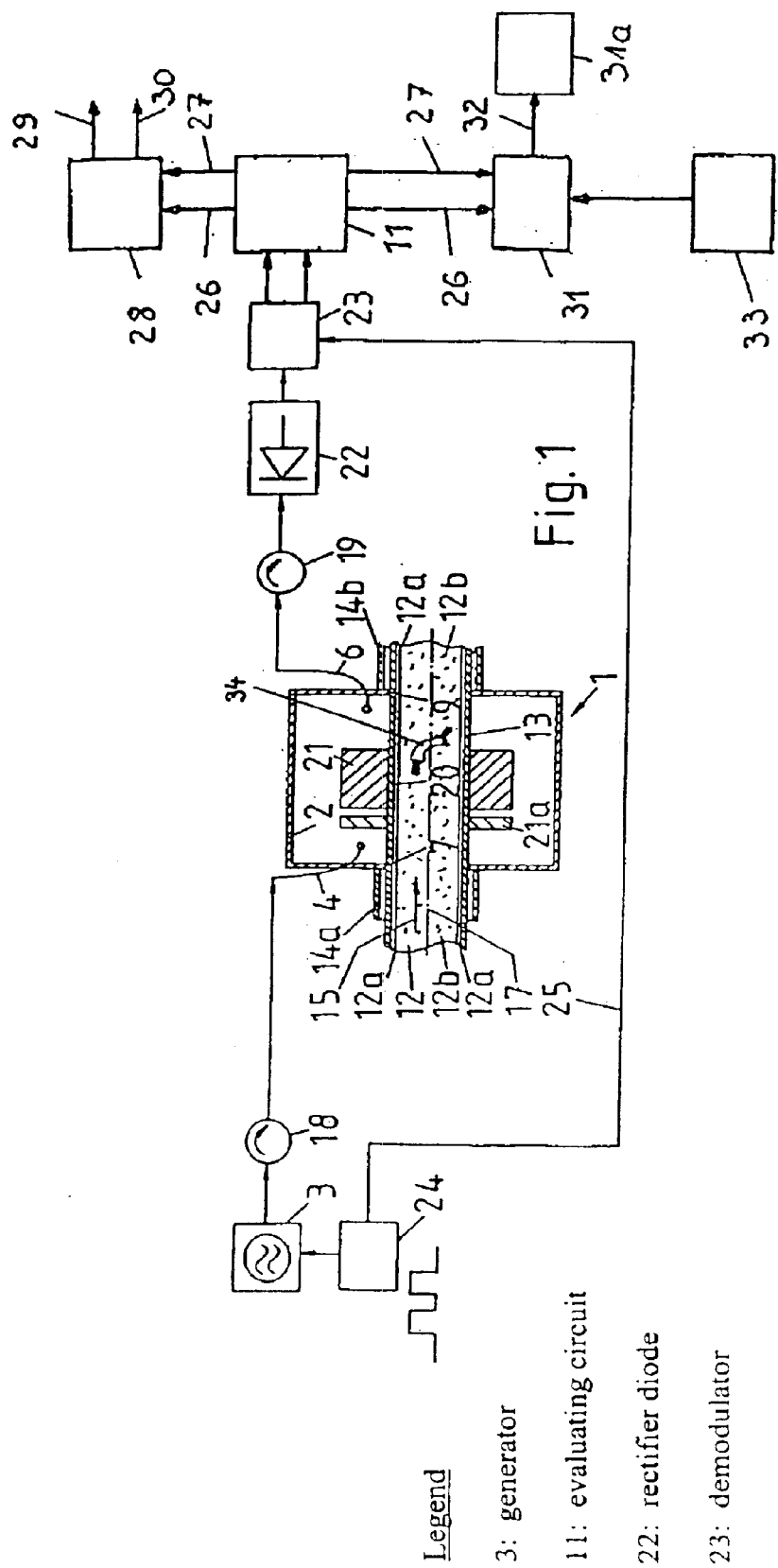
FIG. 1 is a fragmentary partly diagrammatic and partly sectional view of a novel apparatus which constitutes a modification of the apparatus disclosed and shown in published German patent application Serial No. 197 05 260 A1 and can be utilized for the detection of the presence of impurities simultaneously with a determination of density and moisture content in a continuous rod-like tobacco filler in accordance with a method embodying one presently preferred form of the invention.

The apparatus which is shown in FIG. 1 comprises a microwave generator 3 which cooperates with a frequency regulator 24 serving to ensure that the generator 3 generates a field of microwaves having a frequency which varies cyclically and at frequent intervals between a first value f1 and a second value f2. The microwaves are transmitted to a resonator arrangement 1 (hereinafter called resonator) by way of an uncoupling or decoupling unit 18 and an antenna 4.

The decoupling unit 18 serves to ensure that the microwaves being reflected by the resonator 1 cannot disturb the generator 3.

A second antenna 6 couples the microwaves out of the resonator 1 and conveys them to a rectifier diode 22 by way of a second decoupling or uncoupling unit 19. The diode 22 transmits an output signal which is essentially proportional to the microwave output being supplied thereto, and such output signal is transmitted to a demodulator 23. The latter also receives (at 25) signals from the frequency regulator 24. The demodulator 23 utilizes the regulating signals supplied at 25 to divide the output signals supplied by the rectifier diode 22 into a first group which is transmitted to an evaluating circuit 11 when the generator 3 transmits microwaves having a first frequency f1 and into a second group which is transmitted to the evaluating circuit 11 when the generator 3 transmits microwaves having a second frequency f2. The transmission of first and second microwaves from the diode 22 to the evaluating circuit 11 takes place separately. The corresponding curves are shown in the coordinate systems of FIGS. 3, 4 and 5.

The evaluating circuit 11 determines two characteristic values or magnitudes of the microwave field which develops in the resonator 1, namely the average values of and the differences between the two output signals. Signals 26 and 27, respectively representing the average value and the ascertained value of the difference, are transmitted to a first computer 28 as well as to a second computer 31.

The first computer 28 ascertains, on the basis of the signals 26 and 27, the moisture content (see the output 29) and the density (see the output 30) of tobacco in the rod-like filler 12b contained in the continuous cigarette rod 12 being advanced along an elongated path having a portion extending through the resonator 1. The outputs 29 and 30 of the first computer 28 transmit signals to a control circuit (not shown in FIG. 1) which controls the making of the cigarette rod 12.

The second computer 31 monitors the signals 26 and 27 to ascertain whether or not the characteristics of such signals are within an acceptable range. Signals denoting such range are stored in a memory 33 which is connected with the second computer 31. If the monitored signals 26 and 27 are not within the prescribed range, the second computer 31 transmits a signal at 32, and such signal denotes the presence of an impurity (second material) 34 in the cigarette rod portion then advancing through the resonator 1.

The signal furnished by the output 32 of the second computer 31 is transmitted to a suitable segregating device 31a which expels or extracts or ejects the foreign material 34 from the filler 12b or which ejects the impurity 34 together with the corresponding section of such filler. For example, the rod 12 can consist of a line or row of discrete cigarettes of unit length or multiple unit length, and the ejector 31a then segregates the respective discrete cigarette from the path leading satisfactory discrete cigarettes to the next processing station (e.g., to a packing machine or to a so-called tipping machine which serves to turn out filter cigarettes). A suitable ejector which can be utilized (at 31a) in conjunction with the apparatus of FIG. 1 is disclosed, for example, in commonly owned published German patent application Serial No. 198 06 125 A1.

The presence of second (foreign) material including that of the impurity 34 is ascertained in parallel with the determination of the density (30) and of the moisture content (29) of the filler 12b in the running (one-piece or composite) cigarette rod 12. However, it is equally possible to utilize the improved method and apparatus solely for the transmission (when necessary) of signals (at 32) from the computer 31 to the segregating means 31a, i.e., to omit or to deactivate the computer 28.

The resonator 1 comprises a metallic housing 2 having an inlet 7 and an outlet 9 for a tubular guide 13 defining a path for the advancement (see the arrow 15) of the cigarette rod 12 (or a series of discrete cigarettes) therethrough. The rod 12 (or each discrete cigarette of the series) includes a tubular envelope or wrapper 12a of cigarette paper and the aforementioned rod-like tobacco filler (e.g., a filler consisting of or containing shredded tobacco leaves). The housing 2 includes tubular extensions 14a, 14b respectively projecting counter to and in the direction (arrow 15) of advancement of the cigarette rod 12. The purpose of these extensions is to prevent uncontrolled propagation of microwaves out of the housing 2 of the resonator 1.

The actual resonator element 21 surrounds the tubular guide 13 in the housing 2 and includes or is associated with a tuning disc 21a. The parts 21 and 21a can be made of a ceramic or a plastic material having a high relative permittivity. The resonator element 21 has an axial (central) bore or hole 20 for reception of the tubular guide 13. This dielectric resonator element can be omitted, i.e., the housing 2 can serve as a cavity resonator. Reference may be had, for example, to the commonly owned German patent application Serial No. 198 54 550 A1.

When the apparatus of FIG. 1 is in use, the resonator 1 develops in the housing 2 (due to excitation via antenna 4) a standing microwave field having an excitation frequency. If the resonator 1 employs a dielectric resonator element 21, the microwave field is concentrated primarily in the interior of the resonator. On the other hand, if one utilizes a cavity resonator (e.g., a resonator of the type disclosed in the aforementioned German patent application Serial No. 198 54 550 A1), the developing microwave field fills up the entire interior of the resonator 1. In either event, a portion of the microwave field extends through the tubular guide 13 and into the cigarette rod 12. The standing microwave field which develops in the resonator 1 initiates (in the antenna 6) the development of a microwave oscillation which is propagated to the rectifier diode 22 via decoupling element 19.

The amplitude of the standing microwave field which develops in the resonator 1, and hence the amplitude of microwave oscillation which is being propagated via antenna 6, depends upon the difference between the excitation frequency and the resonance frequency of the resonator and upon the band width of the resonator. Such parameters will be explained in greater detail with reference to FIG. 2. Both parameters (i.e., the amplitude of the standing microwave field and the amplitude of microwave oscillation) are influenced by interaction between the cigarette rod 12 and the microwave field. Therefore, the amplitudes of the standing microwave fields which develop in the resonator 1 at successive frequencies f1 and f2 are different and are also subjected to different influences by the advancing cigarette rod 12. Consequently, the two amplitudes, and more particularly their average value 26 and difference 27 determined by the evaluating circuit 11, furnish indications or information not only as regards the presence or absence of impurities (foreign bodies or second material) 34 but also as concerns the density of tobacco (see the output 30 of the computer 28) and the moisture content of tobacco in the rod-like filler 12b of the tobacco rod 12 (outlet 29 of the computer 28).

Figure 2:
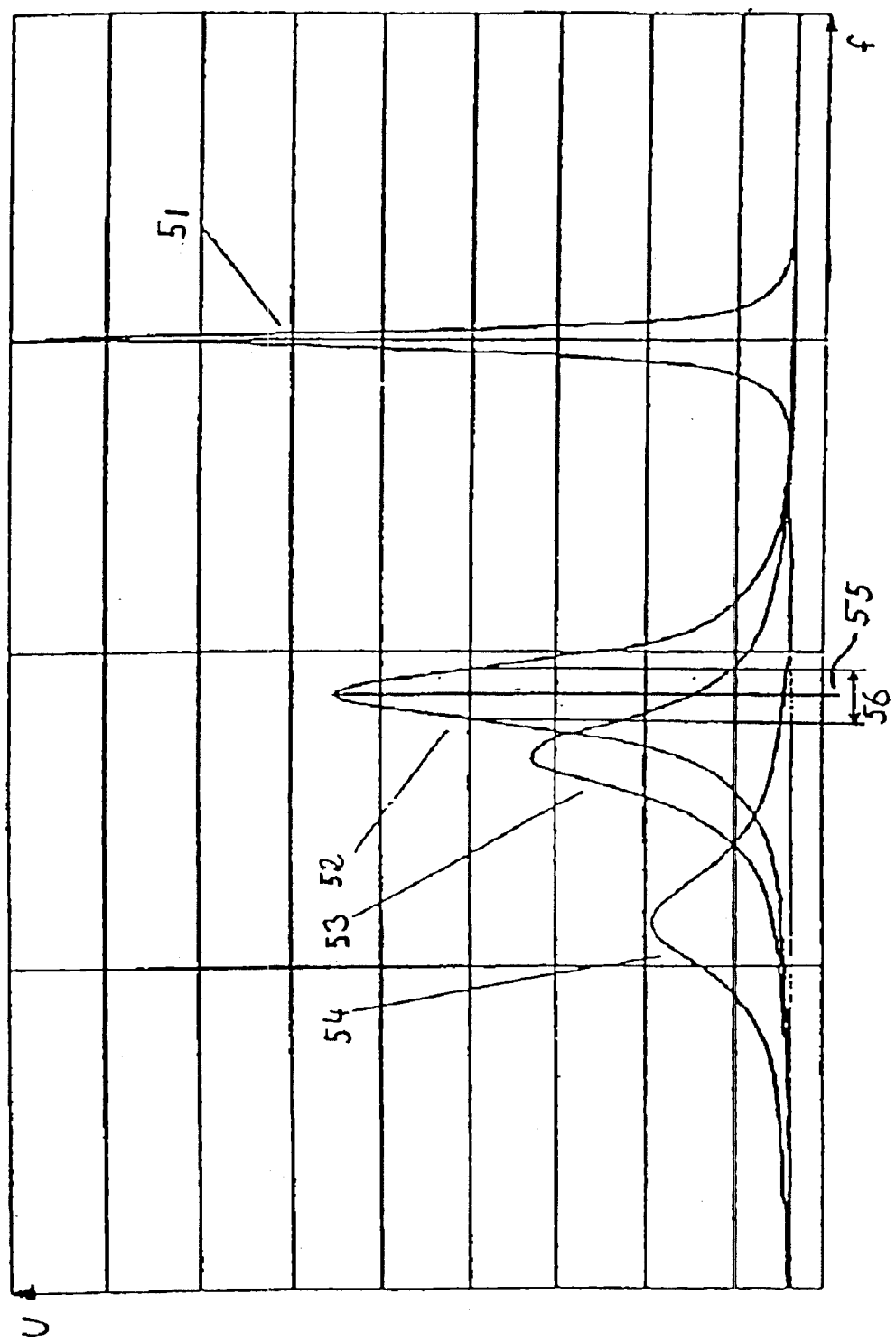
FIG. 2 shows a coordinate system with resonance curves of a resonator which is utilized to monitor the density and the moisture content of a primary material, such as tobacco in a cigarette rod.

The resonance curves 51 to 54 of the type shown in the coordinate system of FIG. 2 develop when a resonator of the aforedescribed character receives microwaves having different frequencies f while the output remains unchanged and the transmission output U coupled out of the resonator is plotted as a function of the frequency f. When the resonator is empty, the resonance curve is that shown at 51, namely a curve which is determined solely by the characteristics of the resonator. In response to fillings of different kinds, for example, with tobacco having varying densities and/or moisture contents, there develop the curves 52, 53, 54 which depart from the curve 51, namely because, in addition to being determined by the resonator characteristics, they are also determined or influenced by the characteristics of the material or substance in the tubular cigarette paper wrapper 12a. Each of the resonance curves can be unequivocally described by two characteristics or parameters, namely by their resonance frequency (shown at 55 on the curve 52) at which one measures the maximum transmission output U, and by their band width, namely the distances between the frequencies at both sides of the maxima, i.e., at which the transmission output U has dropped to 70% of the maximum; this is shown at 56 in connection with the curve 52. In order to measure these two characteristic parameters or values, it is customary to supply to the resonator seriatim microwaves of constant output at, for example, one hundred different frequencies f, to ascertain the tranmission output U at such frequencies f and to utilize such data to mathematically ascertain the two parameters. Furthermore, if one follows the prior art proposals, the thus obtained actual values of the two parameters or the variations (changes) of the two parameters are being resorted to in order to calculate the density of the primary material and the moisture content of such material. On the other hand, the method of the present invention involves utilizing the actual values of such parameters to reach conclusions concerning the presence or absence of impurities (foreign bodies and/or substances) in the mass of primary or first material.

Figure 5:
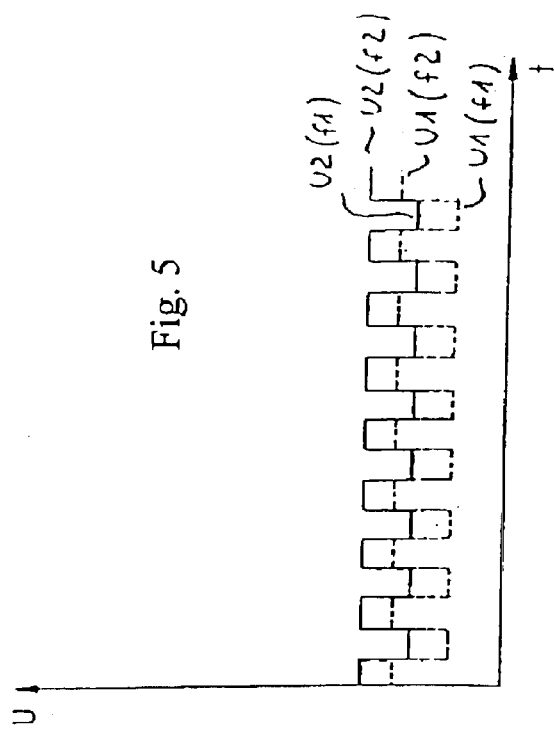
FIG. 5 shows a further coordinate system wherein the curves denote additional steps of evaluating resonance curves of the type shown in FIG. 2.
Figure 4:
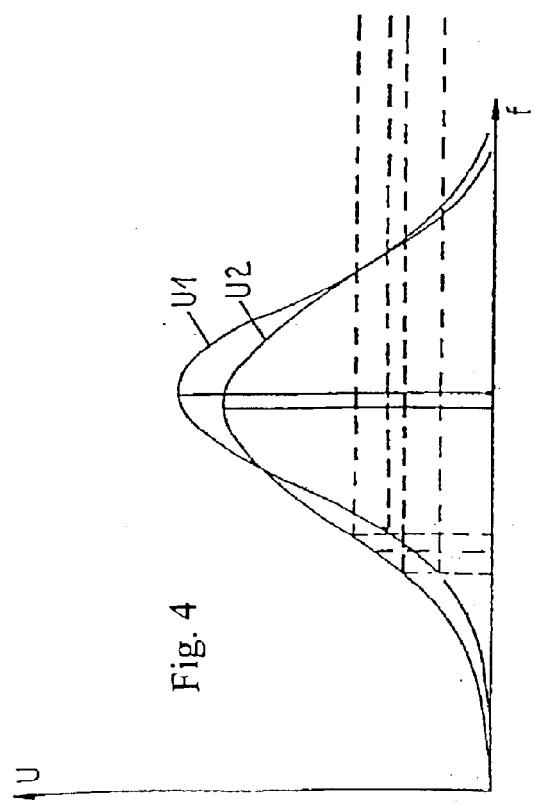
FIG. 4 illustrates another coordinate system wherein the curves denote certain other steps of evaluating resonance curves of the type shown in FIG. 2.
Figure 3:
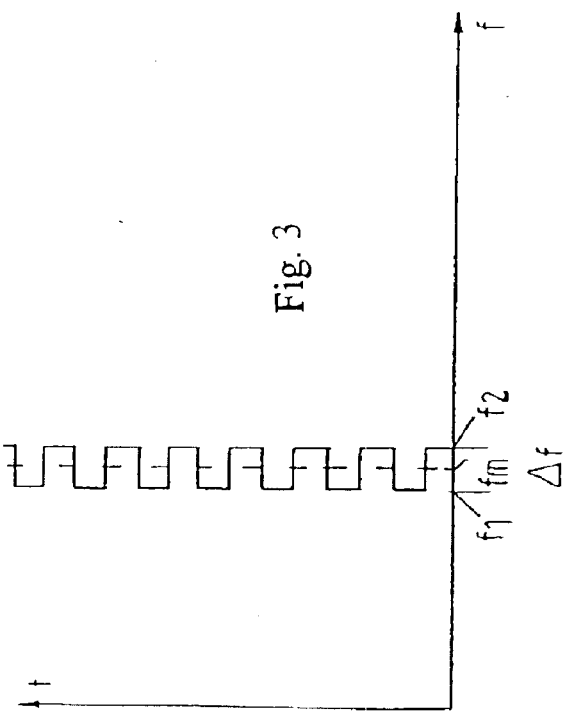
FIG. 3 illustrates a coordinate system wherein the curves denote certain steps of evaluating resonance curves of the type shown in FIG. 2.

A method which can be carried out rapidly and serves to ascertain the characteristic values of resonance curves of the type shown in FIG. 2 by resorting, for example, to the apparatus of FIG. 1 can be practiced in a manner to be described with reference to FIGS. 3 to 5. Referring to FIG. 3, a resonator is alternatingly supplied, in rapid sequence and with a constant output, microwaves at frequencies f1 and f2. These microwaves are arranged symmetrically with reference to (about) a median frequency fm and differ from each other by a value Δf. FIG. 4 illustrates two resonance curves U1 and U2 for an empty resonator and for a resonator which is filled with primary material, respectively. The two curves differ from each other in frequency and in band width. Such curves are shown in FIG. 4 solely for the sake of better understanding of the improved method because, in actual practice, these curves need not be ascertained in their entirety. As shown in FIG. 5, one measures, in rapid sequence, the transmission output at the frequencies f1 and f2, namely the values U1 (f1) and U1 (f2) for the resonance curve U1 of FIG. 4, and the values U2(f1) and U2(f2) for the curve U2 of FIG. 4.

In comparison with the band widths of the resonance curves U1 and U2, the distance Δf of the frequencies f1 and f2 from each other is very small, i.e., much smaller than the ratio shown in FIG. 5 greatly exaggerated for the sake of clarity. Thus, the average or median value of the measured transmissions corresponds to the flank heights of resonance curves at the average frequency fm, whereas the difference between the transmissions corresponds to the flank slopes of the resonance curves at the median frequency fm. The flank height and the flank slope represent two characteristic values of the resonance curves. In accordance with the teachings of prior art, the actual values of these parameters are utilized as starting values for a determination of density and moisture content of the primary material. On the other hand, and as taught in accordance with this invention, the actual values of the just mentioned parameters are being resorted to in order to draw conclusions concerning the presence or absence of impurities (foreign substances) in the primary material (e.g., shredded tobacco).

In lieu of digital switching of the starting frequencies f1 and f2 in a manner as described hereinbefore with reference to FIGS. 3 to 5, one can also resort—for example—to a sinusoidal frequency modulation without necessitating appreciable modifications of the improved method and apparatus.

Figure 6:
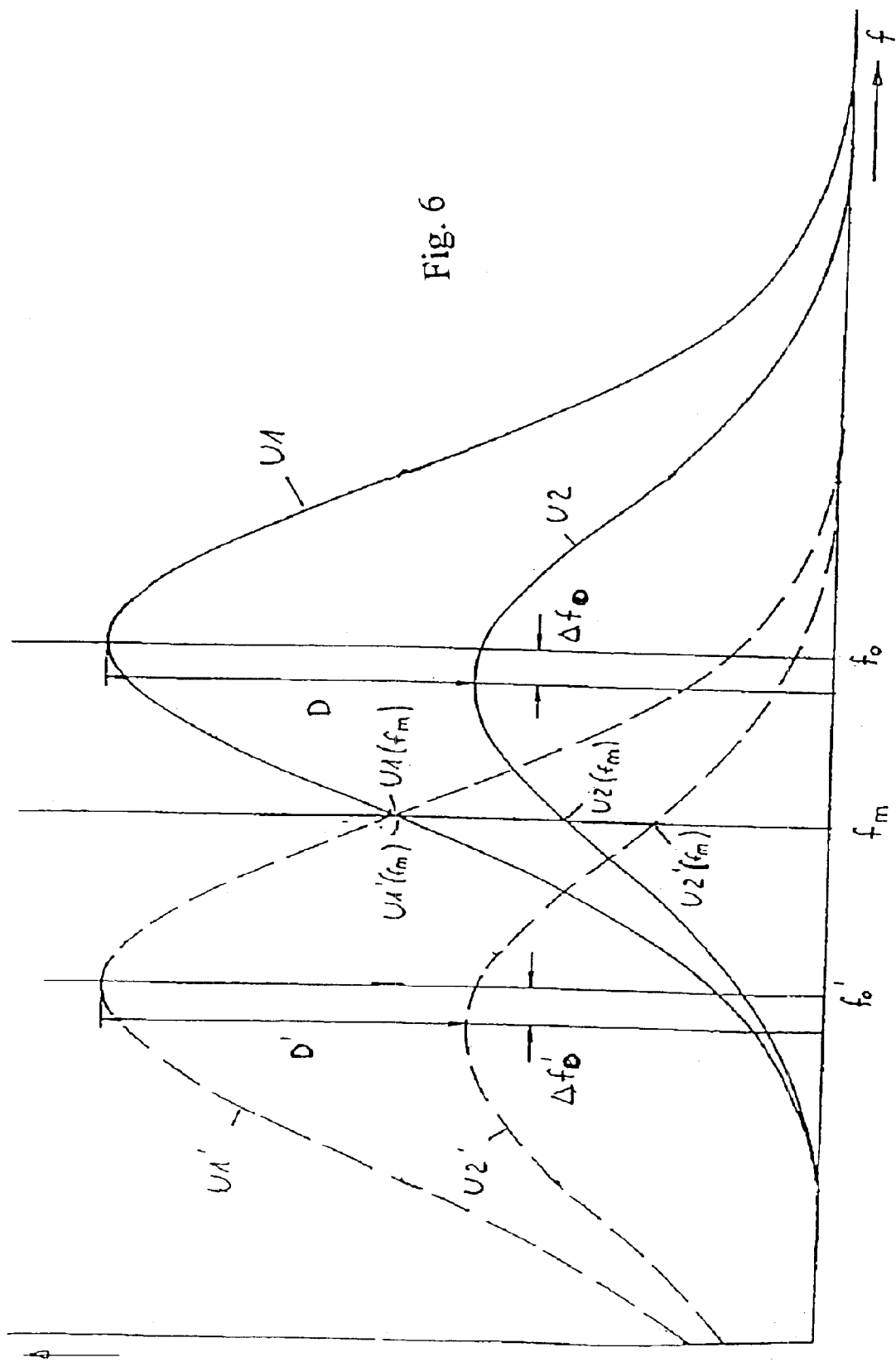
FIG. 6 shows a coordinate system with curves denoting certain steps of a modified method of ascertaining two characteristics of a microwave field which is influenced by a primary material and potential impurities therein.

That embodiment of the improved method which is about to be described with reference to FIG. 6, and serves to ascertain two characteristic values of a microwave field, is practiced by resorting to two resonators which can be or which are being influenced by the primary material one after the other. A related or analogous method is disclosed, for example, in the commonly owned German patent application Serial No. 196 25 944 A1. When not contacted by primary material, the two resonators are represented by the resonance curves U1 and U1' having resonance frequencies fo and fo', respectively, which are shifted relative to each other.

The two resonators are supplied microwaves of identical outputs and at a frequency fm which is midway between the frequencies fo and fo'. Due to the essentially symmetrical progress of the resonance curves as concerns their respective resonance frequencies fo and fo', the transmission outputs U1 (fm) and U1'(fm) measured behind the unoccupied resonators are identical. When the resonators are influenced by a primary material, one obtains the respective resonance curves U2 and U2' which are damped relative to the curves U1 and U1' by the respective factors D and D' and are frequency shifted by the amounts Δfo and Δfo', respectively. The transmissions U2(fm) and U2'(fm) which are ascertained in the occupied condition are no longer equal and are reduced when compared with U1 (fm) and U1'(fm). The resulting average value of the transmissions and the difference between such transmissions again represent two characteristic values of the microwave field and, in accordance with prior art teachings, their actual values are utilized to ascertain the density and/or the moisture content of the primary material. In accordance with the method of the present invention, the actual values of such parameters are utilized to ascertain the presence or absence of impurities (foreign bodies) in a primary material, e.g., in tobacco or filter material for tobacco smoke.

The just described measurement can be readily modified in a sense that the difference or distance between the resonance frequencies fo, fo' of the two resonators is much greater than illustrated and in that, in lieu of a measurement frequency fm, a different frequency is selected for each resonator, namely a frequency which is close to the resonator frequency (fo, fo') of the corresponding resonator. FIG. 6 does not take into consideration that the primary material is effective with the two resonators interchangeably at timely spaced intervals; thus, the situation which is actually shown develops when the two resonators are simultaneously influenced by one and the same section or portion of the primary material; this corresponds to actual application of the method. In an apparatus which is utilized for the practice of the improved method, such circumstances can be established in that the measurement signals furnished by the resonator which is first to interact with the primary material are electromagnetically delayed in any suitable manner.

Figure 7:
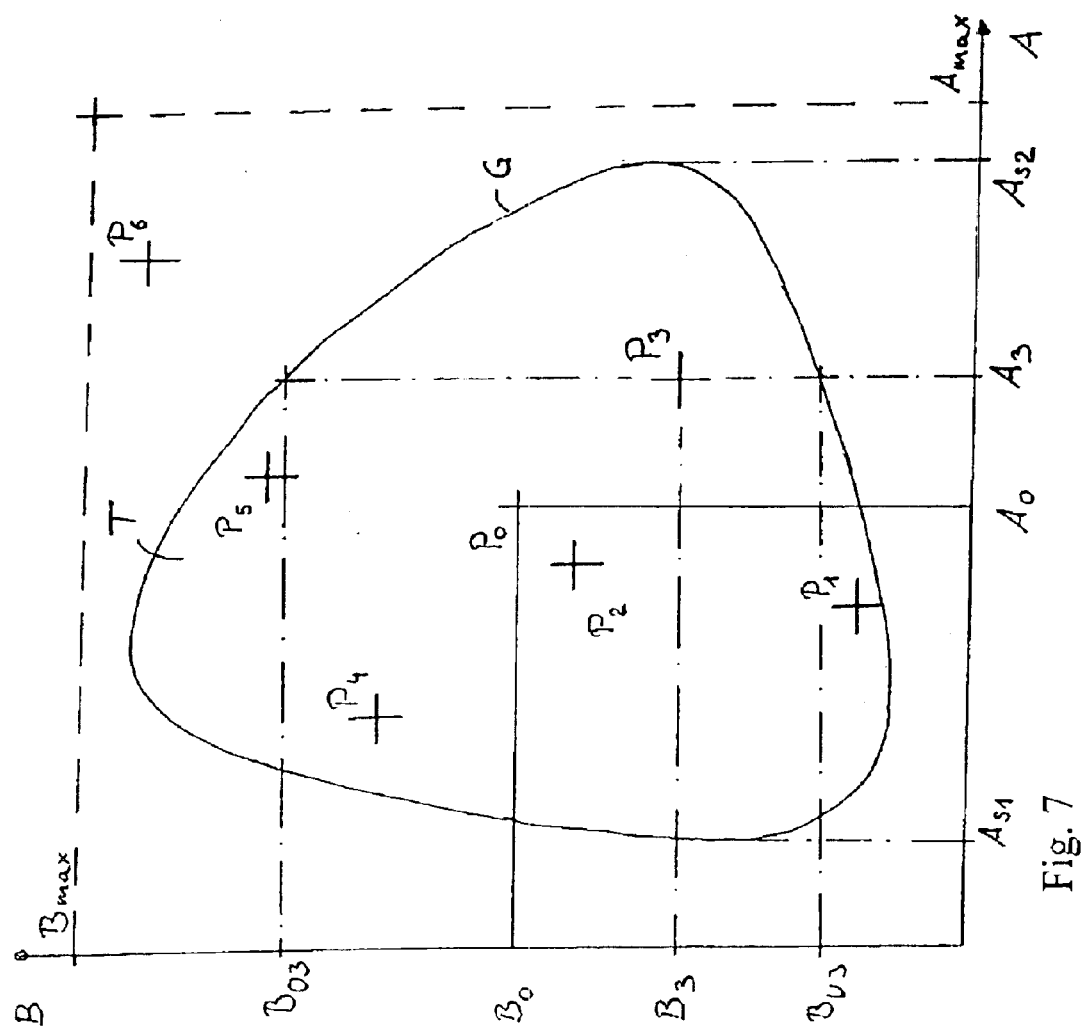
FIG. 7 illustrates, in a coordinate system, a theoretical plane determined by the values of two parameters of the microwave field, a closed boundary line being applied to circumscribe the area for recognition or detection of impurities.

FIG. 7 illustrates a theoretical plane which is established by the possible values A and B of characteristic values of the microwave field. Each couple of values (A; B) which was ascertained, for example, in accordance with one of the aforediscussed methods, provides or constitutes one point in such plane. When the apparatus which is utilized for the practice of the improved method is started, one proceeds first with a so-called learning process which involves conveying through the apparatus a reference quantity (sample mass) of primary material which is devoid of impurities. If the method is practiced in conjunction with a cigarette making machine, e.g., a machine known as PROTOS 90 which is distributed by the assignee of the present application, a cigarette rod is conveyed through the apparatus for a period of one minute at a speed of 10 meters per second. Since, in accordance with the aforedescribed methods, one pair of values of characteristic parameters is ascertained per millimeter of advancement of the cigarette rod, the learning process with a sample mass involves a recording of approximately 600,000 pairs of values of which (for the sake of clarity) only five pairs A1; B1 to A5; B5 are actually shown in FIG. 7, namely at the points P1 to P5. The respective average values of the pairs, designated Ao resp. Bo, are calculated, and the point Po corresponding to the pair Ao; Bo constitutes the center of a value range T in which the value pairs taken up in the course of the aforementioned learning process are located. The illustrated plane is limited by the possible maximum values Amax, Bmax of the two parameters.

The pairs of values of the two parameters which are ascertained in the course of the learning process define the permissible range T. This range is surrounded by a closed boundary line G which encompasses essentially all of the ascertained value pairs. In the simplest case, such boundary line can constitute a circle with a center at Po of the range T. The radius of the circle is selected in such a way that all of the points are located within its confines and some of the points are barely located within such confines.

In order to arrive at a more accurately conforming boundary line G, one can proceed, for example, in accordance with a mathematical determination in a manner as will be described hereinbelow.

A mathematical function S(A, B) is employed to assign a number S to each pair of values (A; B). A satisfactory function is, for example, $$S = S(A, B) = \sum_{i,j} a_{i,j} \cdot (A - A_0)^i \cdot (B - B_0)^j$$

wherein $a_{i,j}$ are parameters which render it possible to conform the function to the outline of the area T. In order to carry out such conforming step, one first obtains the sum QS of the squared function values S2 for all value pairs (A; B) in accordance with the equation $$QS = \Sigma S^2(A,B)$$

and, by varying the parameters $a_{i,j}$, the function values are optimized in such a way that the sum QS is reduced to a minimum. The next step involves the definition of a threshold value $S_G$ for the function S; this value is selected in such a way that the function S(A,B) for all value pairs (A;B) is less than $S_G$ for all value pairs (A;B). The boundary curve G then represents the quantity of all of the points $P_G$ for the corresponding value pairs $(A_G;B_G)$ for which one relies upon the equation $$S(A_G, B_G) = S_G.$$

The boundary curve G which is shown in FIG. 7 can be arrived at, for example, for a boundary value $S_G$=5, with the parameters $$a_{i,j} = \begin{pmatrix} 0 & 0 & 0,5 \\ 0 & 0,3 & 0,2 \\ 0,5 & 0,2 & 0,04 \end{pmatrix}.$$

For example, if one is to ascertain, for a point $P_3$ which has been determined by the values $A_3$ and $B_3$, whether or not such point is located within the permissible value range T, one can proceed as follows:

The first step involves a determination of the smallest value $A_{S1}$ and the maximum value $AS_2$ within the value range T, and such values are utilized as the boundary values for the value $A_3$. If the value $A_3$ is between the two boundary values (see FIG. 5), the point $P_3$ can be located within the value range T. Otherwise, this could be excluded and a signal would be generated. In the next step, one ascertains the minimum value $B_{U3}$ and the maximum value $B_{O3}$; these values are located at the level of the value $A_3$ within the range T, and they are utilized as boundary values for the value $B_3$. If (and as shown in FIG. 7) the value $B_3$ to be tested is located between these two boundary values, the point $P_3$ is also located within the range T; otherwise, a signal would have to be generated.

The additionally illustrated point $P_6$ is clearly outside of the range T. The presence of corresponding values of both magnitudes thus results in the generation of a signal.

The preceding description merely refers to certain embodiments of the present invention. For example, it is to be understood that the improved method can be put to use in connection with the monitoring of many other types of primary (first) materials which can be examined with microwaves for the presence or absence of impurities and/or materials other than the primary material. Furthermore, the characteristic values of the microwave field which are to be ascertained can include phase rotation of a microwave field during advancement through a resonator or during irradiation of a primary material to be tested by an oriented radiation field. It is also possible to ascertain the phases and the amplitudes of microwaves which are reflected by resonators or by irradiated primary material.

In accordance with the present invention, the actual values of the microwave field generated by the resonator 1 or an equivalent resonator can constitute real values, such as amplitude and phase, as well as the dimensions of a component which guides the microwave field, such as, for example, the resonance frequency and the band width of a resonator in which the microwave field expands.

The method of the present invention is based upon the recognition or discovery that the aforediscussed dielectric properties of tobacco and/or filter material for tobacco smoke are quite different from those of many other materials. As far as the impurities are concerned, they are most likely to constitute substances which are used on a large scale (extensively) because they are more or most likely to come in contact with tobacco or filter material for tobacco smoke. As a rule, or in most instances, the impurities are or include fragments or particles of a metallic or plastic material.

The influence of metals upon a microwave field is basically different from that of tobacco or filter material for tobacco smoke. Thus, the high conductivity of metals causes a short circuiting of the electric component by the electromagnetic field. This entails pronounced reflections and straying of microwaves.

As far as the plastic materials which are used in the relevant field or fields are concerned, they are normally optimized for the purpose of not accepting any water because their ability to absorb water could result in an undesirable dependency of their electrical and/or mechanical properties upon the climate. Therefore, the relative permittivity and loss factors of the plastic substances are quite different from those of tobacco or filter material for tobacco smoke each of which can absorb and retain a high percentage of water.

A machine which can turn out a continuous cigarette rod as well as a series of discrete plain cigarettes is disclosed, for example, in U.S. Pat. No. 4,281,670 granted Aug. 4, 1981 to Heitmann et al. A machine which can turn out a continuous rod of wrapped filter material for tobacco smoke as well as a series of discrete filter rod sections is disclosed in U.S. Pat. No. 4,412,505 granted Nov. 1, 1983 to Häusler et al.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of the above outlined contribution to the art of locating and disposing of impurities in masses of tobacco particles or the like and, therefore, such adaptations should and are intended to be comprehended within the meaning and range of equivalence of the appended claims.

What is claimed is:

1. A method of testing a mass consisting at least primarily of a first material for the presence of at least one second material, comprising the steps of:
   establishing and maintaining a microwave field in a microwave resonator;
   introducing the mass into the range of the microwave field so that the field is influenced by the mass; and
   analyzing the influence of the mass upon the microwave field, including:
      simultaneously measuring the actual values of a first and a second characteristic of the microwave field,
      selecting an acceptable, two dimensional value range for the actual values,
      ascertaining whether the actual values are within the acceptable range, and
      generating signals when the actual values are outside of the acceptable range.

2. The method of claim 1, wherein the acceptable range encompasses measured values of first and second characteristics of the microwave field when the field is influenced by a mass containing only the first material.

3. The method of claim 1, wherein the actual values are outside of the acceptable value range, to thus initiate the generation of signals, when the mass being introduced into the range of the microwave field contains the at least one second material.

4. The method of claim 1, wherein the mass includes a stream and said introducing step includes moving the stream through the microwave field.

5. The method of claim 1, wherein the mass consists at least of the first material, of a wrapper for the first material, and potentially of at least some second material randomly distributed in the first material.

6. The method of claim 1, wherein the first material is a material of the tobacco processing industry.

7. The method of claim 6, wherein the first material is a smokable material.

8. The method of claim 6, wherein the first material is filter material for tobacco smoke.

9. The method of claim 1, further comprising the steps of:
   conveying the mass through the microwave field along a predetermined path;
   subdividing the mass in said path into a plurality of sections; and
   utilizing said signals to segregate from said path those sections of the mass the introduction of which into the range of the microwave field resulted in the generation of signals.

10. The method of claim 1, wherein said introducing step includes imparting to the mass the shape of a stream and conveying the steam in a predetermined direction along a path extending through the microwave field, confining the stream in a wrapping material upstream of the microwave field, as seen in said direction, and subdividing the wrapping material and the first material therein into a succession of discrete sections, and further comprising the step of utilizing said signals to remove from said path discrete sections containing said second material.

11. The method of claim 10, wherein each discrete section includes a rod-shaped smokers' product.

12. The method of claim 1, wherein said step of selecting an acceptable value range for the actual values includes introducing into the microwave field a sample mass which is devoid of the at least one second material, examining the sample mass while within the microwave field, and utilizing the examining step to select said acceptable value range.

13. The method of claim 12, wherein the sample mass contains a tubular envelope.

14. The method of claim 1, further comprising the step of utilizing said actual values of said first and second characteristics of the microwave field for a determination of a characteristic of the mass other than potential presence of at least one second material.

15. The method of claim 14, wherein the first material contains tobacco and said characteristic other than the potential presence of at least one second material includes at least one of the density and moisture content of tobacco.

16. Apparatus for testing a mass consisting at least primarily of a first material for the presence of impurities, comprising:
   means for establishing and maintaining a microwave field in a microwave resonator;
   means for moving at least one of the mass and the microwave field relative to the other so that the field is influenced by the mass; and
   means for analyzing the influence of the mass upon the field, including:
      means for simultaneously measuring the actual values of first and second characteristics of the field,
      means for selecting an acceptable, two dimensional value range for the actual values,
      means for ascertaining whether the actual values are within the acceptable range, and
      means for generating signals when the actual values are outside of the acceptable range as a result of the influence of impurities upon the microwave field.

17. The apparatus of claim 16, wherein said moving means includes means for moving an elongated flow of mass along an elongated path including a portion extending through the microwave field.

18. The apparatus of claim 16, further comprising means for segregating, in response to said signals, from the mass portions containing at least one impurity.

19. The apparatus of claim 16, wherein the first material is a material of the tobacco processing industry.

20. The apparatus of claim 16, further comprising means for processing said actual values for the determination of at least one characteristic of first material other than the presence or absence of impurities.

* * * * *